(12) United States Patent
Flohr et al.

(10) Patent No.: US 6,307,909 B1
(45) Date of Patent: Oct. 23, 2001

(54) METHOD FOR IMAGE RECONSTRUCTION IN A COMPUTED TOMOGRAPHY DEVICE

(75) Inventors: Thomas Flohr, Uehlfeld; Bernd Ohnesorge, Erlangen; Karl Schwarz, Roth, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/450,389

(22) Filed: Nov. 29, 1999

(30) Foreign Application Priority Data

Nov. 27, 1998 (DE) .............................................. 198 54 917

(51) Int. Cl.[7] ...................................................... A61B 6/03
(52) U.S. Cl. .................................. 378/4; 378/8; 378/901
(58) Field of Search ........................... 378/4, 8, 15, 901

(56) References Cited

U.S. PATENT DOCUMENTS 5,299,248   3/1994   Pelc ........................................... 378/5
5,640,436   6/1997   Kawai et al. .
5,953,388  * 9/1999   Walnut et al. ............................. 378/4

FOREIGN PATENT DOCUMENTS 0 300 143   6/1981   (EP) .

* cited by examiner

Primary Examiner—David V. Bruce
(74) Attorney, Agent, or Firm—Schiff Hardin & Waite

(57) ABSTRACT

In a method for image reconstruction in a computed tomography (CT) device, which picks up projections of a region located in a measuring field of an examination subject having an extent which exceeds this measuring field, the projections are identified in which the measuring field was exceeded, and extrapolated measurement points representing the detected cut-off projections, are added to the series of "actual" measurement points in such a way that each series of measurement points representing a detected projection is completed in an optimally realistic manner, and begins and ends with a measurement point whose measurement value is substantially zero.

15 Claims, 11 Drawing Sheets

DETECTOR ROWS $3_1$ TO $3_3$

REFERENCE ROW $3_4$

METHOD FOR IMAGE RECONSTRUCTION IN A COMPUTED TOMOGRAPHY DEVICE

BACKGROUND OF THE INVENTION

1. Field of the Invention

The present invention relates to a method for image reconstruction in a computed tomography (CT) device having a radiation source that can be displaced relative to an examination subject and a detector system for radiation emanating from the radiation source that registers projections, in different angular positions of the radiation source relative to the examination subject, of a region of the examination subject located within the measuring field, whose extent exceeds the measuring field, a projection being represented by a series of measuring points, each of which is characterized by a channel number and a measurement value.

2. Description of the Prior Art

In CT imaging systems the geometry of the measuring arrangement consisting of the radiation source, for instance an x-ray source, and the detector system defines a cylindrical measuring field centered on a rotational axis, around which the radiation source and possibly the detector system rotate in order to register projections. If parts of the examination subject that is to be projected are situated outside this measuring field, sharp image artifacts arise in the form of extensive bright regions and streaks at the margin of the measuring field near where the measuring field is exceeded. These artifacts are caused by measurement values at the beginning and/or the end of the projections that differ greatly from zero. The measuring field usually lies centered in a gantry opening. The circumstances of the measuring field being exceeded thus can be caused by either unusually large subjects or by mis-positioned subjects.

There are known dedicated methods for image reconstruction from segmented projections, such as iterative methods or wavelet methods, but these are characterized by high computing outlay.

It is also taught by U.S. Pat. No. 5,640,436 to counteract artifacts that are caused by the subject exceeding the measuring field by applying measuring data acquired by means of X-radiation of different energy levels.

In addition, U.S. Pat. No. 5,299,248 and European Application 0 030 143 teach methods to expand projections in which the measuring field is traversed by extrapolation such that each series of measurement points representing a detected projection is complete, beginning and ending with a measurement point whose measurementvalue is approximately zero. Despite this improvement, the image quality frequently leaves something to be desired.

SUMMARY OF THE INVENTION

An object of the present invention is to provide a method of the above-descrbed type that permits correction of the image artifacts that arise due to the subject exceeding the measuring field and that offers a good quality of the reconstructed images.

The above object is achieved is achieved in accordance with the principles of the present invention in a method for image reconstruction in a CT device wherein a radiation source, or at least the focus thereof, is rotated around a system axis and an examination subject so as to irradiate the examination subject from different projection angles, and a detector system receives the attenuated radiation and generates signals which form respective data sets (projections) for each projection angle, wherein the projections are used to generate an image of a region of the examination subject located in the measuring field, with the examination subject also exceeding (extending out of) the measuring field, and wherein each projection is represented by a series of measurement points, each of which is characterized by a channel number and a measurement value. Projections wherein the examination subject exceeds the measuring field are detected (identified), and extrapolated measurement points, representing the identified projections, are added to the series of "actual" measurement points in order to complete each series of actual measurement points, so that each series of measurement points representing a detected projection begins and ends with a measurement point having a measurement value which is substantially zero, The extrapolation can occur by means of at least one of two techniques. In the first technique, the extrapolation ensues so that measurement points which are to be added are acquired by mapping the measurement points representing the projection in a rectangular coordinate system having a measurement value axis and a channel number axis, and reflecting a number of successive measurement points at the beginning and/or at the end of the series of measurement points representing the projection at a line proceeding through the first or last measurement point respectively of that series which is parallel to the measurement value axis. A subsequent reflection is also made along a line proceeding through the first or last measurement point respectively of the series of points representing the projection parallel to the channel number axis of the rectangular coordinate system. In a second extrapolation technique, the extrapolation is accomplished using reference data for the measuring field that is present without gating of the radiation.

The inventive method is based on the expansion and extrapolation of the measured projections. The expansion and extrapolation can be limited to those projections having detectable exceeding of the measuring field and should ensure a drop in the measurement values to zero at the beginning and end of the expanded series of measurement points representing the projection.

By the inventive method it is possible to maintain the diagnostic value of even those images which were registered with the subject exceeding measuring field and to avoid a repetition of the examination with a modified position of the examination subject, such as may be necessary due to inadequate image quality. Besides the high quality of correction that can be achieved, the described method is distinguished by the possibility of simple realization and by low computing outlay.

The use of the inventive method permits an effective enlargement of the measuring field defined by the geometry of the CT device and is particularly appropriate for "compact" CT devices having relatively small measuring fields, but also for systems having larger measuring fields.

Particularly good results are achieved with the inventive method, because the extrapolation, a symmetric extrapolation according to a first alternative, occurs such that the added measurement points are acquired by reflecting a number of successive measurement points at the beginning or the end of the series of measurement points that represent the projection, mapped in a rectangular coordinate system having a measurement value axis and a channel number axis, at a line proceeding through the first and last measurement points of the series of points representing the projection, parallel to the axis of the coordinate system corresponding to the measurement value. A subsequent reflection also occurs at a line proceeding through the first and last measurement points of the series of points representing the projection parallel to the axis of the coordinate system corresponding to the channel number. In this way, the projections are expanded by realistic data, with the result that the noise behavior also is successfully maintained for the extrapolated regions of the projections.

A high image quality is likewise achieved when, according to a second inventive alternative, wherein the extrapolation is accomplished using reference data for the measuring field that is present without gating of the radiation, since it is then also guaranteed that the data added in the course of the extrapolation will very closely approximate the actual relations.

According to a variation of the invention, projections encompassing an exceeding of the measuring field, these projections being used to perform the extrapolation, are detected by considering threshold values. If the average value of the measurement values of a number of successive measurement points $N_{th,sco}$ preferably in immediate succession at least at the beginning or at the end of a series of points representing a projection, exceeds a threshold value, then a projection is assumed to be one in which the measuring field was exceeded. The detection of projections encompassing an exceeding of the measuring field is thus possible in a very simple manner that is not very intensive in terms of computing.

In an embodiment of the invention, the selection of the extrapolation parameters, that is, the number of measurement points to be added to the detected projections, is performed by estimating the measure of the exceeding of the measuring field. This procedure is also not very computationally intensive.

In a particularly preferred embodiment of the invention, in order to realize an optimally smooth transition of the extrapolated measurement points to zero, a weighting of the extrapolated measurement points with an attenuation function occurs, which guarantees such a transition. Although the number of extrapolated measurement points that are added is usually such that the length limitation of the convolution is not exceeded, in certain circumstances it may be appropriate to add such a number of extrapolated measurement points that the length limit of the convolution is exceeded, in a variant of the invention, since a particularly good image quality at the margin of the measuring field is then achieved, at least given a moderate exceeding of the length limit of the convolution.

Since several processing steps are necessary for the reconstruction of an image, in order to minimize the computing outlay the extrapolation and the addition of extrapolated measurement points occur at an optimally late time in the sequence of the image reconstruction, thereby limiting the computing outlay, which is increased by the addition of measurement points, to only a few subsequent processing steps. According to another variant of the invention, the extrapolation and the addition of measurement points occur in the sequence of the image reconstruction immediately prior to the filtering of the data with a convolution kernel.

The occurrence of the measuring field being exceeded need not necessarily be arise by the circumstances of the examination itself, i.e., an unavoidable or unintentional exceeding of the measurement field. According to a variant of the invention, it can also be caused intentionally by gating the radiation emanating from the radiation source to form a reduced measuring field that suffices for the imaging of a diagnostically relevant region. The inventive method then is used to reconstruct a partial subject within the gated reduced measuring field from segmented projections. A high image quality is guaranteed here as well, and at the same time, a reduction of the radiation dose delivered to the examination subject is achieved. In addition, the computing outlay is reduced according to the lower number of channels that corresponds to the reduced measuring field. The image reconstruction preferably occurs only for a reconstruction measuring field situated within the reduced measuring field. The "safety gap" to the reduced measuring field which is present in this case then guarantees an adequate image quality in the reconstruction measuring field up to its margin.

In a preferred embodiment of the invention, the extrapolation ensues using reference data that were measured prior to the examination for the measuring field, without gating of the radiation. This guarantees that the extrapolation approximates the real relations very closely.

According to another preferred embodiment of the invention, the extrapolation can be measured by applying reference data relating to the measuring field that is present without gating of the radiation, the data being measured at the same time as the measurement points relating to the reduced measuring field. This can ensue by means of a detector system comprising several rows of detector elements that are consecutively arranged in the direction of the system axis of the CT device, with one of the rows of detector elements being used for determining the reference data.

In order to guarantee a smooth transition between measured and extrapolated measurement points, in an embodiment of the invention a scaling of the reference data takes place to the level of the measurement values of the measurement points measured in the reduced measuring field.

The extrapolation based on measured reference data instead of a numerical extrapolation is particularly advantageous when only the diagnostically relevant region changes from pick-up to pick-up, while the region surrounding the relevant region remains essentially the same.

It is thus clear that the inventive method allows the correction of the image artifacts arising due to the measuring field being exceeded in situations other than when the exceeding of the measuring field occurs unavoidably or unintentionally. The inventive method is suitable for correcting artifacts in the intentional projecting of partial subjects within larger body regions. A measuring field that is reduced due to the correspondingly gated radiation then makes it possible to reduce the radiation dose delivered to the examination subject. Moreover, the computing outlay is lower, though the correction algorithm of the inventive method nevertheless ensures a high diagnostic image quality in the reduced measuring field. This inventive method is also suitable for image reconstruction for reduced measuring fields having a lower channel number given small subjects (e.g. 25 cm head measuring field). It is also advantageous that the inventive method makes it possible to integrate the extrapolation process into the image reconstruction efficiently.

DESCRIPTION OF THE PREFERRED EMBODIMENTS

Figure 1:
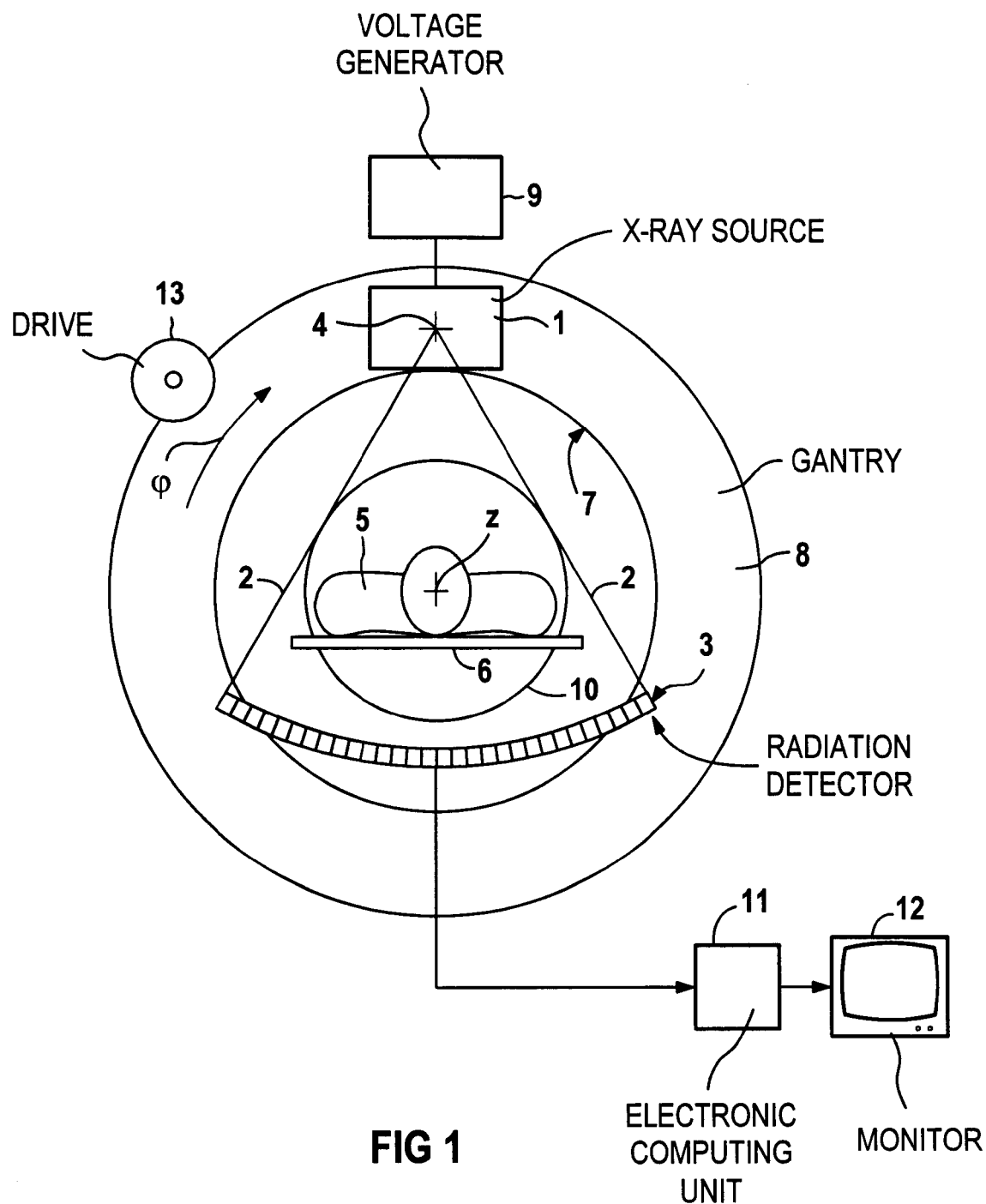
FIG. 1 is a schematic block diagram of a CT device in which the inventive method for image reconstruction is used.

The radiographic CT device illustrated in FIG. 1 has a measuring unit including an X-ray source 1 that emits a fan-shaped X-ray beam 2 and a radiation detector 3 that is composed of one or more rows of individual detectors, for instance 512 individual detectors, that are arranged in succession in the direction of the system axis. The focus of the x-ray source 1 from which the X-ray beam 2 emanates is referenced 4. The examination subject 5 (a human patient in the exemplary embodiment) lies on a support table 6 extending through the measuring opening 7 of a gantry 8.

The radiation source 1 and the detector 3 are secured at the gantry 8 opposite one another. The gantry 8 is mounted such that it can be rotated around the z axis or the system axis of the CT device, referenced z, and it is rotated about the z axis in the $\phi$ direction for scanning the examination subject 5, specifically through an angle amounting to at least 180° plus the fan angle (aperture angle of the fan-shaped X-ray beam 2). The X-ray beam 2 emanating from the X-ray source 1 that is driven by means of a voltage generator 9 covers a measuring field 10 of circular cross-section.

Projections are registered at specific angle positions of the measuring unit 1, 3, with the corresponding data proceeding from the detector 3 to an electronic computing unit 11, which reconstructs the attenuation coefficients of the image points of an image point matrix from the series of measurement points corresponding to the projections, and reproduces them on a monitor 12 on which images of the transirradiated slices of the examination subject 5 appear. Each projection p(l,k) is allocated to a specific angle position, that is, to a projection angle l, and comprises a number of measurement points corresponding to the number of detector elements, i.e., the channel number, to which points the corresponding measurement values are respectively allocated, k being the channel number indicating from which detector element the measurement value originates.

Since the detector 3 can contain several lines, it is possible to project several slices of the examination subject 5 at once if necessary, with a number of projections corresponding to the number of active detector lines being picked up per projection angle.

The drive 13 that is allocated to the gantry 8 can cause the gantry 8 to continuously rotate, and an additional drive can be provided that enables a relative displacement, in the z direction, between the support table 6 and thus the examination subject 5, and the gantry 8 with the measuring unit 1, 3, it is also possible to perform spiral scans.

As described above, in situations as illustrated in FIG. 1 in which the dimensions of the examination subject 5 are such that the subject exceeds the measuring field 10, artifacts arise. Such artifacts also arise when the examination subject 5 does not necessarily exceed the measuring field 10 by virtue of his dimensions, but rather is disadvantageously positioned on the measuring table 6 such that an exceeding of the measuring field 10 occurs. To eliminate artifacts such as this, the electronic computing unit 11 applies the inventive method of image reconstruction that is detailed below.

According to this method, first projections are detected in which an exceeding of the measuring field is presumed.

To detect whether the measuring field is exceeded in a projection p(l,k) with a total of $N_S$ measurement points (k=0(1)($N_S$−1)), an interval of $N_{th,sco}$ measurement points at the beginning and end of the projection is considered. If the average value $M_A(l)$ or $M_E(l)$ according to the equations (1a) and (1b), of the first or last $N_{th,sco}$ measurement points lies above a predefined threshold value $S_{th,sco}$ it is assumed that the examination subject exceeds the measuring field:

$$M_A(l) = \frac{1}{N_{th,GCO}} \cdot \sum_{k=0}^{N_{th,GCO}-1} p(l,k) \tag{1a}$$

$$M_E(l) = \frac{1}{N_{th,SCO}} \cdot \sum_{k=0}^{N_{th,SCO}-1} p(l, N_S - 1 - k) \tag{1b}$$

A reasonable parameter choice for $N_{th,sco}$ is $N_S/150$, for example. For $S_{th,sco}$ the attenuation value of approximately 5 mm $H_2O$ can be used.

Figure 2:
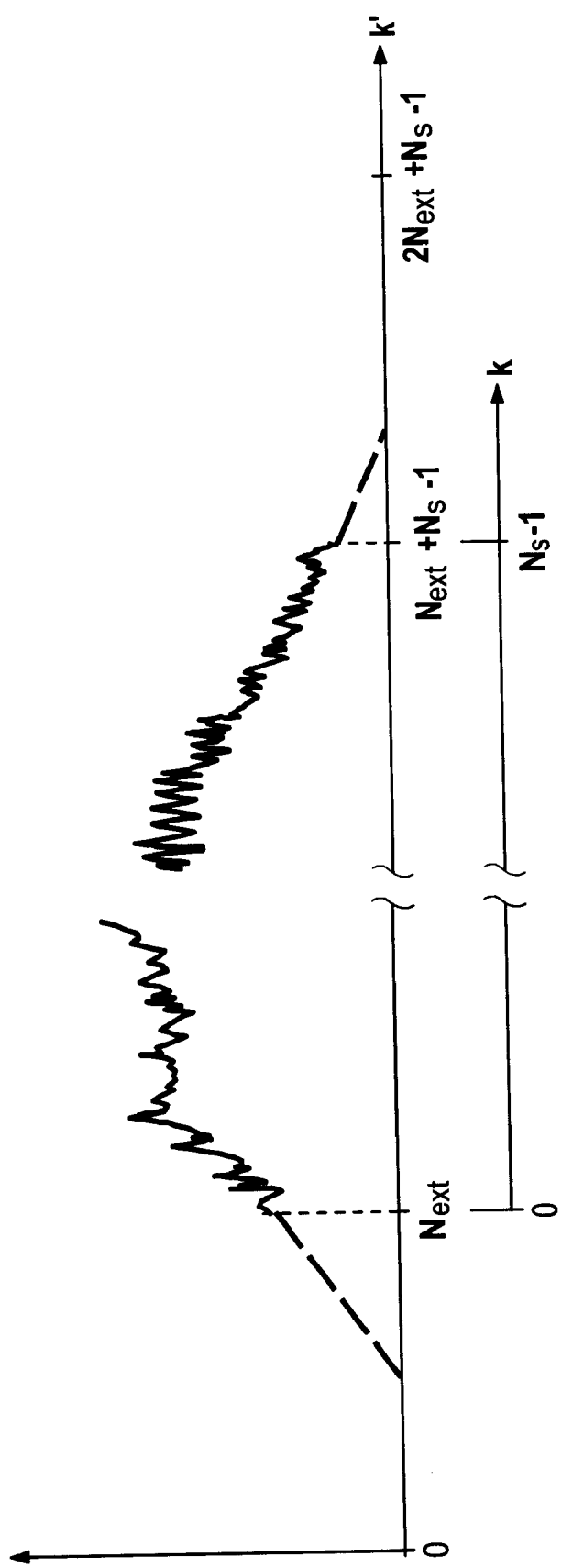
FIGS. 2 to 4 respectively show diagrams illustrating the different approaches to the extrapolation of measurement points in the inventive method.

The first step of the actual correction is the symmetrical expansion of the projections p(l,k) wherein the measuring field is exceeded by $N_{ext}$ measurement points with the attenuation value zero at the beginning and end of the projection, as is illustrated in FIG. 2. The expanded projection $p_{ext}(l,k')$ having the channel index k'=0(1)($N_S$+2$N_{ext}$−1) derives from the equation (2):

$$p_{ext}(l,k') = \begin{cases} 0, & k' = 0(1)(N_{ext}-1) \\ p(l, k' - N_{ext}), & k' = N_{ext}(1)(N_S + N_{ext} - 1) \\ 0, & k' = (N_S + N_{ext})(1)(N_S + 2N_{ext} - 1) \end{cases} \tag{2}$$

The appropriate selection of the expansion parameter $N_{ext}$ is detailed later.

In the following step of the correction the determination of the "measurement values" of the "Measurement points" that were added to the projections wherein the measuring field is exceeded ensues by extrapolation. Although there are not actual measured data involved, the terms "measurement points" and "measurement values" are used here.

The extrapolation of the measurement points must guarantee a smooth transition of the corresponding measurement values to zero. FIG. 2 illustrates the basic relations for an extrapolation within the intervals at the beginning or the end of a projection with $N_{ext}$ measurement points.

Figure 3:
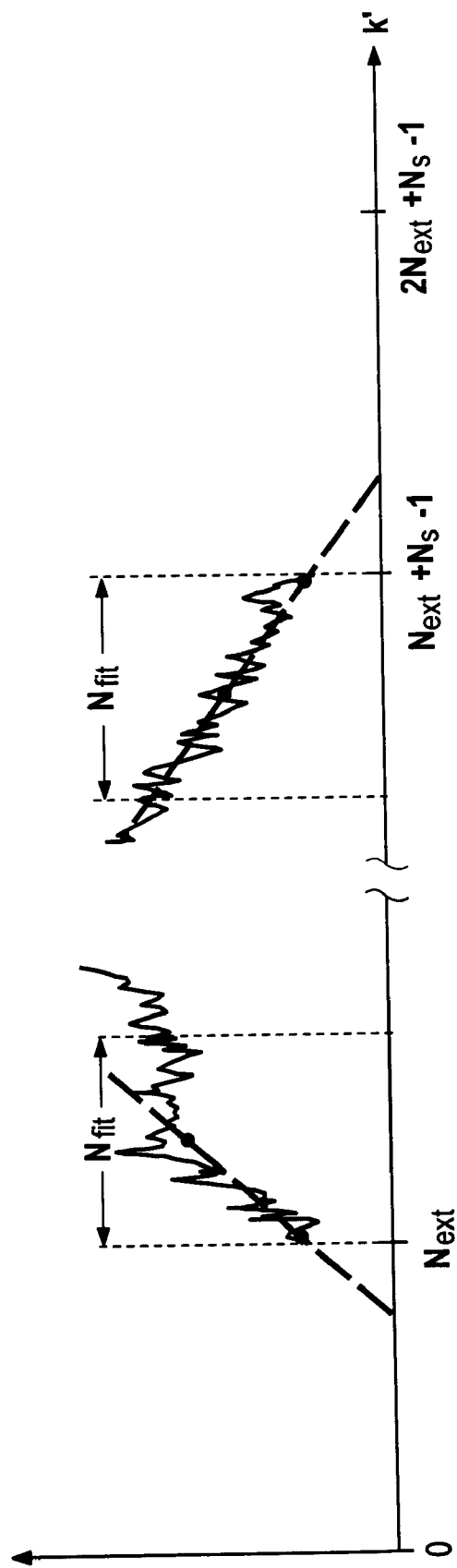

A first possibility for extrapolation is to undertake a linear fit to the first or last measurement points of the projection in the interval k'∈[$N_{ext}$(1)($N_{ext}$+$N_{fit}$−1)], or respectively, k'∈ [$N_{ext}$+$N_S$−$N_{fit}$)(1)($N_{ext}$+$N_S$−1)] as illustrated in FIG. 3. The calculation of the extrapolated regions occurs with the coefficients $c_{0,A}$, $c_{1,A}$, or $c_{0,E}$, $c_{1,E}$, according to equations (3a) and (3b):

$$\tilde{p}_{ext}(l,k')=c_{0,A}(l)+c_{1,A}(l)\cdot k', \ k'=0(1)(N_{ext}-1) \tag{3a}$$

$$\tilde{p}_{ext}(l,k')=c_{0,E}(l)+c_{1,E}(l)\cdot k', \ k'=(N_S+N_{ext})(1)(N_S+2N_{ext}-1) \tag{3b}$$

The calculation of the coefficients can occur by a calculation of the minimum sum of the quadratic derivatives. A simpler alternative is to calculate the average value of the measurement points in the window of the width $N_{fit}$ at the ends of the projections. Together with the first or last valid measurement point, the average values then determine the coefficients for the linear fit.

Analogously to the described linear fit, it is also possible to perform a fit of higher order (e.g. a parabolic fit) of the $N_{fit}$ measurement points $K' \in [N_{ext}(1)(N_{ext}+N_{fit}-1l)]$ at the beginning of the projection orof the measurement points $k' \in [(N_{ext}+N_S-N_{fit})(1)(N_{ext}+N_S-1)]$ at the end of the projection. For a parabolic fit considered here as an example, the extrapolation equations (4a) and (4b) apply:

$$\tilde{p}_{ext}(l,k')=c_{0,A}(l)\ 30\ c_{1,A}(l)\cdot k'+c_{2,A}(l)\cdot(k')^2, k'=0(1)(N_{ext}-1) \quad (4a)$$

$$\tilde{p}_{ext}(l,k')=c_{0,E}(l)+c_{1,E}(l)\cdot k'+c_{2,E}(l)\cdot(k')^2, k'=(N_S+N_{ext})(1)(N_S+2N_{ext}-1) \quad (4b)$$

The calculation of the coefficients can in turn occur by determining the minimal sum of the quadratic derivatives or by calculating the average values within two respective windows having $N_{fit}$ measurement points at the ends of the projections. The parabolic coefficients then result from the average values and the first or last valid measurement point of the projection.

Figure 4:
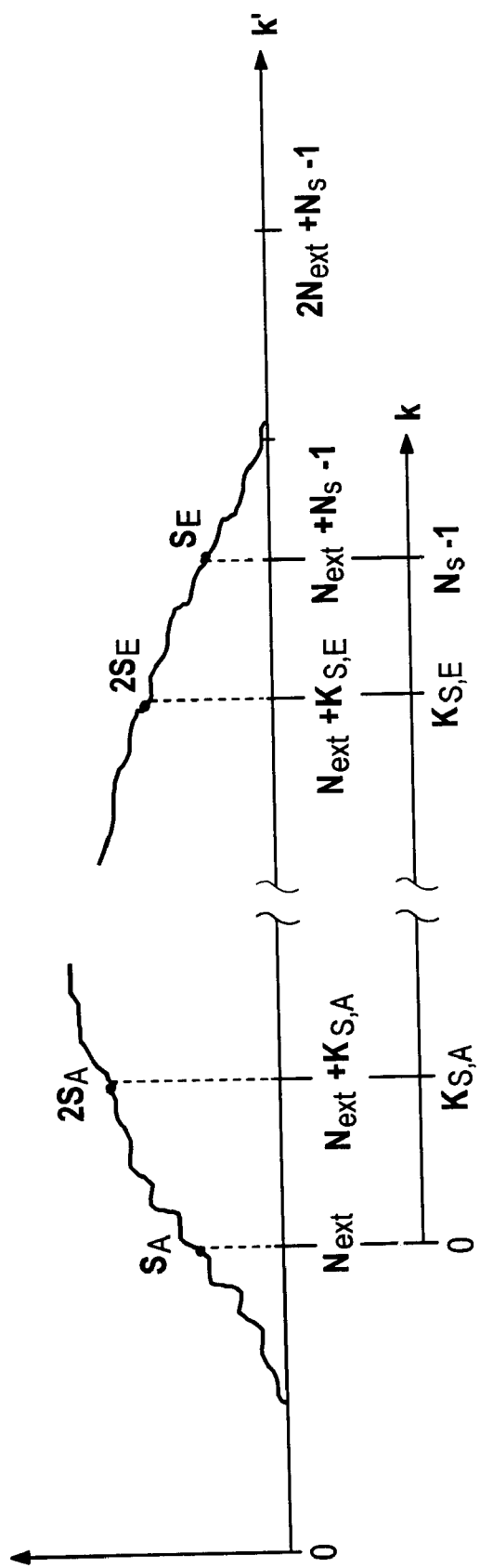

A particularly preferred type of extrapolation is the symmetric extrapolation illustrated in FIG. 4.

In this approach, the valid measurement points at the beginning or end of the projection are copied by reflection respectively at the first or last measurement point of the projection, as an extension of the measured projection into the extrapolation interval. The equations (5a) and (5b) describe the extrapolation ule of this approach, which is distinguished by a very low computing outlay. Equation (5a) relates to the beginning of the projection; equation (5b) relates to the end of the projection:

$$\tilde{p}_{ext}(l,N_{ext}-k)=2S_A(l)-p(l,k) k=1(1)K_{S,A} \quad (5a)$$

$$\tilde{p}_{ext}(l,2N_S+N_{ext}-2-k)=2S_E(l)-p(l,k),\ k=(N_S-2)(-1)K_{S,E} \quad (5b)$$

$S_A$ and $S_E$ are the respective values of the first and last valid measurement points of the projection in question $p(k)$, with $S_A=p(0)$, $S_{E=p(NS}-1)$. $K_{S,A}$ and $K_{S,E}$ are the respective indices of the first and the last measurement points, which exceed the respective thresholds $2S_A$ and $2S_E$ with $p(K_{S,A})>2S_E$. The threshold indices must be respectively limited to $K_{S,A} \leq N_{ext}$ and $K_{S,E} \leq N_S-N_{ext}-1$. To reiterate, FIG. 4 illustrates the extrapolation defined by the equations (5a) and (5b) with measurement point reflection, wherein it can be seen that reflection occurs first at lines respectively proceeding through the first and last measured measurement points parallel to the axis of the rectangular coordinates system of FIG. 4 corresponding to the measurement value, and then at lines respectively proceeding through the first and last measured measurement points parallel to the axis corresponding to the channel numbers k and k', respectively.

The approach of symmetric extrapolation has the advantage over the other two described approaches of a constant transition to the projection ends. Moreover, the noise behavior of the projection is maintained in the extrapolation interval.

In order to guarantee smooth transitions of the extrapolated measurement points to zero, the extrapolation interval is also weighted according to equations (6a) and (6b) with respective attenuation functions $w_A(k')$ and $w_E(k')$. Boundary values $WA(0)=0$, $w_A(N_{ext}-1)=1$, $w_E(N_S+2N_{ext}-1)=0$ and $w_E(N_S+N_{ext}-1)=1$ preferably apply to the attenuation functions:

$$p_{ext}(l,k')=\tilde{p}_{ext}(l,k')\cdot w_A(k'),\ k'=0(1)(N_{ext}-1) \quad (6a)$$

$$p_{ext}(l,k')=\tilde{p}_{ext}(l,k')\cdot w_E(k'),\ k'=(N_S+N_{ext})(1)(N_S+2N_{ext}-1) \quad (6b)$$

For $w_A(k')$ and $w_E(k')$, cosine-shaped functions according to equations (7a) and (7b) can be used:

$$w_A(k') = \left(\sin\frac{k'\cdot\pi}{2(N_{ext}-1)}\right)^{\tau_{\cos}} \quad (7a)$$

$$w_E(k') = \left(\cos\frac{(k'-N_S-N_{ext})\cdot\pi}{2(N_{ext}-1)}\right)^{\tau_{\cos}} \quad (7b)$$

The cosine-shaped attenuation vectors can be calculated and stored in advance for pre-specified extrapolation parameters. For example, the parameter $\tau_{\cos}$ is selected in an interval $\tau_{\cos}\in[0.5;3]$.

In the interest of an optimized image quality for examination subjects with sharply varying structures at the measuring field margin (e.g. shoulder, skull in the reduced measuring field), it is appropriate to estimate the amount (in dimensional terms) that the subject exceeds the measuring field in a relevant projection in order to subsequently adapt the extrapolation parameters for the extrapolation of this projection. The parameters $N_{ext}$ and $\tau_{\cos}$ or the range of the attenuation functions $w_A$ and $w_E$ can be varied dependent on a suitable measure of the exceeding of the measuring field and the subject structure at both projection margins. In the exemplary embodiment, the number of channels in the intervals $[0;K_{S,A}]$ and $[K_{S,E};NT-1]$ and the ratio of the measurement value at the projection margin to the maximum measurement value of the projection, are used as this measure.

In the image reconstruction the series of measurement points representing the projections pass through a chain of several processing steps in the electronic computing unit 11. The last step in the chain before the direct calculation of the CT image, for instance by back-projection, is the filtering of the projections with a convolution kernel having a high-pass character. In the case of the measuring field being exceeded, this is the cause of the arising artefact. In the exemplary embodiment, the extrapolation can occur in the reconstruction chain basically at any time prior to the convolution. In the case of the described exemplifying embodiment, the extrapolation takes place optimally late, that is, directly before the convolution, in order not to unnecessarily increase the data volume that must be processed in the preceding steps, and thus also not unnecessarily increasing the computing outlay.

For the filtering with the convolution kernel, projections of the length $N_S$ must be brought to the convolution length $L_F \geq 2N_S-1$ (convolution length limit) by the addition of measurement points with the value zero in order to avoid over-convolution errors ("aliasing"). The inequality $L_F \geq 2(N_S+2N_{ext})-1$ must apply to the convolution length for the extrapolated projections. In general, the filtering of the projections is performed by multiplying the discrete spectra in the frequency region. The discrete projection spectra are calculated with "Fast Fourier Transformations" (FFTs) of the length, designated $L_{FFT}$. Using the known radix2-FFT, $L_{FFT}$ must satisfy the equation $L_{FFT}=2^{ceil(ld(2NS-1))}$ (ld(x)= logarithm to the base of 2 of x,ceil(x)=x rounded up to the nearest whole number). If the channel number $N_S$ of the projections does not correspond to a power of two, then an extrapolation of the projections in the "difference interval" can occur without an enlargement of the FFT length and tnus of the computing outlay. The limit of the extrapolation range, described by $N_{ext}$, is given by equation (8):

$$N_{ext} = \frac{1}{2} \cdot \left( \frac{L_{FFT}}{2} - N_S \right) \quad (8)$$

If the number of channels of a projection exceeds the length limit of the convolution, the filtering causes overconvolution errors in the margin region of the projections. Typically, such "aliasing" errors are expressed in the reconstructed images as a decrease in the CT value level proceeding toward the margin of the measuring field. Should the number of channels of the projections in question lie very close to a power of two, the extrapolation step may require violating the length limit of the convolution with $2(N_S+2N_{ext})-1>L_F$. Since exceeding the measuring field in the projections lead to an increase of the CT value in the outer region of the measuring field, the counteractive effect of the convolution can be exploited for partial compensation. Given a suitable selection of the extrapolation interval, represented by $N_{ext}$, and a moderate crossing of the length limit of the convolution, an outstanding image quality is achieved at the measuring field margin. Artefacts cased by exceeding the measuring field are eliminated, while aliasing artefacts do not appear. It is also possible to avoid increasing the length of convolution $L_F$ and thus to avoid the associated increased computing outlay.

In a second operating mode of the CT device that differs from the one previously described, the correction of artefacts in the intentional capturing of partial subjects within larger body sections occurs according to an expanded method that builds on the method already described; that is, there also occurs an image reconstruction from segmented projection data.

Figure 5:
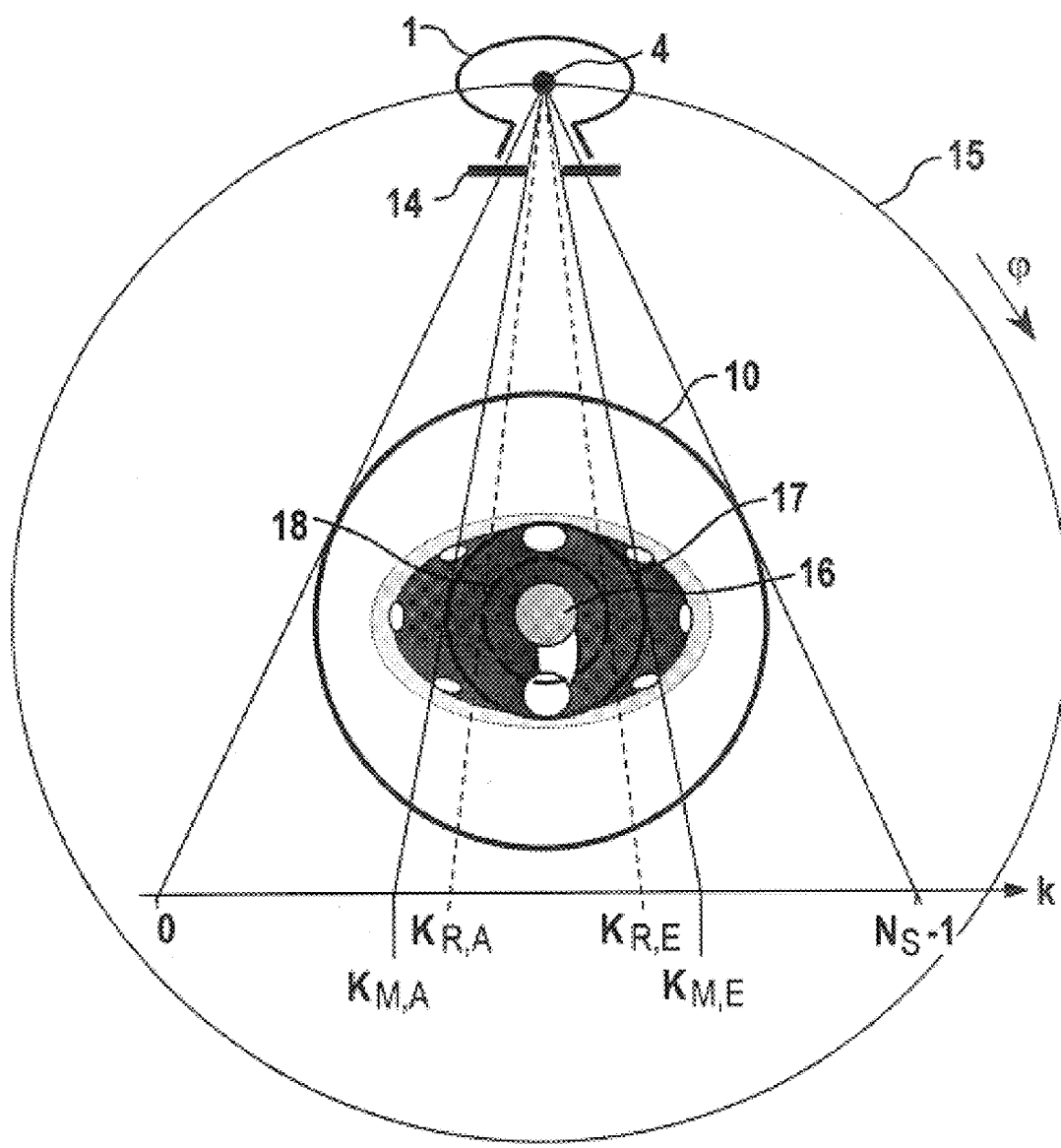
FIG. 5 is a simplified schematic illustration of a CT device that applies the inventive method, in a second operating mode employing a reduced measuring field.

In this second operating mrode, an overtravel of the active measuring field is intentionally caused to be exceeded by, according to FIG. 5, gating the fan-shaped X-ray beam 2 emanating from the X-ray source 1 to a reduced measuring field 17 that suffices for imaging a diagnostically relevant region 16. This gating is performed by means of a diaphragm, preferably a primary ray diaphragm 14 adjacent the X-ray source 1.

According to FIG. 5, for such a reduced measuring field 17, only the channel interval $[K_{M,A}, K_{M,E}]$ of a relevant projection is still covered by valid measurement points. Theoretically, it is possible to reconstruct an image in the entire reduced measuring field 17 using the inventive method. More sensibly, a reconstruction image field 18 is defined within the reduced measuring field 17, which covers the channel interval $[K_{R,A}, K_{R,E}]$ in the projections. Since the image representation is limited to the reconstruction image field 18, the diagnostically relevant region 16 should lie completely within this field. The "safety gap" to the reduced measuring field 17 guarantees an adequate image quality for the diagnostically relevant region 16 in the reconstruction image field 18 up to its margin.

Artefacts and errors in the CT value levels can still be expected within the reconstruction image field 18 due to the abrupt cut-off of the projections at the margin of the reduced measuring field 17. These are prevented by a suitable extrapolation of the data in the channel region outside the reduced measuring field 17. As a rule, the entire examination subject 5 will clearly exceed the reduced measuring field 17. This means it cannot be assumed that an extrapolation can be limited to the "flank" of the projections at the margin of the examination subject 5.

The following describes two examples of approaches to extrapolation that can be selectively activated in the second operating mode. which are expansions of those described in the context of the first operating mode.

Figure 6:
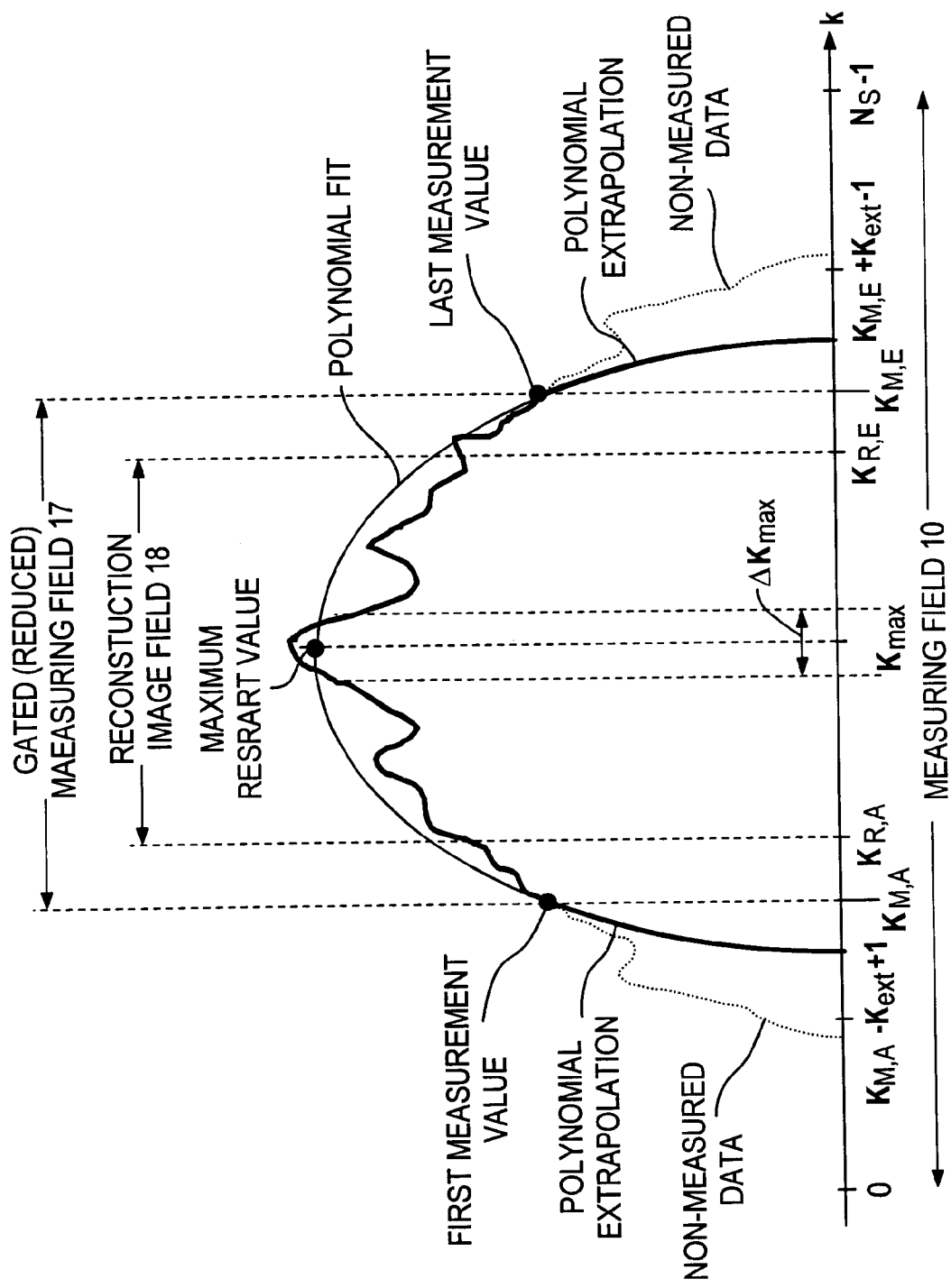
FIG. 6 is a diagram illustrating the extrapolation of measurement points for the operating mode as illustrated in FIG. 5.

The first approach is a polynomial extrapolation. Here, as illustrated in FIG. 6, in the extrapolation intervals $[K_{M,A}-K_{ext}+1; K_{M,A}]$ and $[K_{M,E}; K_{M,E}+K_{ext}-1]$ measurement points are calculated by a parabolic approximation (polynomial fit) of the second order. The parabolic coefficients $c_0(l)$, $c_1(l)$, $c_2(l)$ are determined from three supporting points, namely a first measurement point $p(l, K_{M,A})$, a last measurement point $p(l, K_{M,E})$ and $$\tilde{p}(l, K_{max}(l))$$

by solving the equation system (9). $K_{max}(l)$ is the channel index of the maximum value of the projection 1. The "maximum restart value" is the average value of a symmetrical channel interval of the width $\Delta K_{max}$ about the index $K_{max}(l)$ $$c_0(l)+c_1(l)\cdot K_{M,A}+c_2(l)\cdot K_{M,A}{}^2=p(l,K_{M,A})$$
$$c_0(l)+c_1(l)\cdot K_{max}(l)+c_2(l)\cdot(K_{max}(l))^2=\tilde{p}(l,K_{max}(l))$$
$$c_0(l)+c_1(l)\cdot K_{M,E}+c_2(l)\cdot K_{M,E}{}^2=p(l,K_{M,E}) \quad (9)$$

The measurement points in the extrapolation intervals can then be calculated simultaneously according to the equation (10).

$$\tilde{p}_{ext}(l,k)=c_0(l)+c_1(l)\cdot K+c_2(l)\cdot K^2 \text{ for } k=(K_{M,A}-K_{ext}+1)(1)K_{M,A}, k= K_{M,A}(1)(K_{M,A}+K_{ext}-1) \quad (10)$$

As in the case of the first operating mode, a uniform convergence of the extrapolated data to zero is guaranteed by, for instance, cosine-shaped weightings of the extrapolation intervals according to equations (11a) and (11b) as well as (12a) and (12b).

$$p_{ext}(l,k) = \tilde{p}_{ext}(l,k)\cdot w_A(k), \quad k = (K_{M,A} - K_{ext} + 1)(1)K_{M,A} \quad (11a)$$

$$p_{ext}(l,k) = \tilde{p}_{ext}(l,k)\cdot w_E(k), \quad k = K_{M,E}(1)(K_{M,E} + K_{ext} - 1) \quad (11b)$$

with $$w_A(k) = \left( \sin \frac{(k - K_{M,A} + K_{ext} + 1)\cdot \pi}{2(K_{ext} - 1)} \right)^{T\cos} \quad (12a)$$

$$w_E(k) = \left( \cos \frac{(k - K_{M,E})\cdot \pi}{2(K_{ext} - 1)} \right)^{T\cos} \quad (12b)$$

The width of the extrapolation interval can be selected such that it is possible to use a convolution length $L_{F,M}$ that is reduced compared to the complete projection. If overconvolutions are to be avoided, $L_{F,M} \geq 2(K_{M,E}-K_{M,A}+2K_{ext}+1)$ must apply. As in the first operating mode, a moderate violation of the convolution length limit is possible after the extrapolation.

According to the second approach, the extrapolation takes place outside the reduced measuring field 17 based on measured reference data, preferably in the examination of subregions of a region of the examination subject 5 with moderate variation of the measured examination slice positions in the z direction. Examples of medical applications are cardio examinations or fluoroscopic CT-supported interventional procedures.

In the determination of the reference data, two procedures can be selectively activated.

Figure 7:
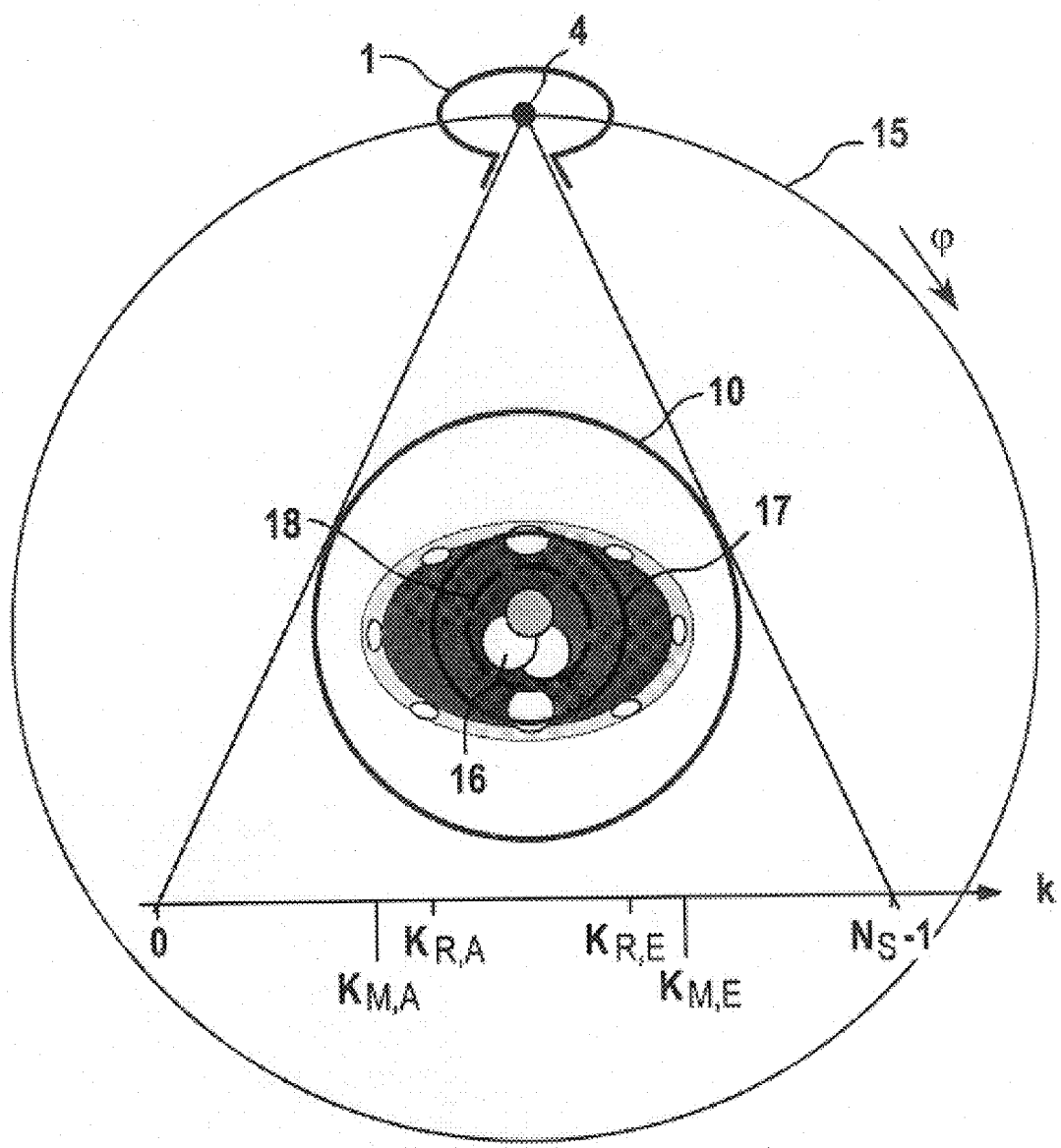
FIGS. 7 and 8 respectively show simplified schematic illustrations of a CT device operating according to the inventive method, in a variation of the second operating mode.
Figure 8:
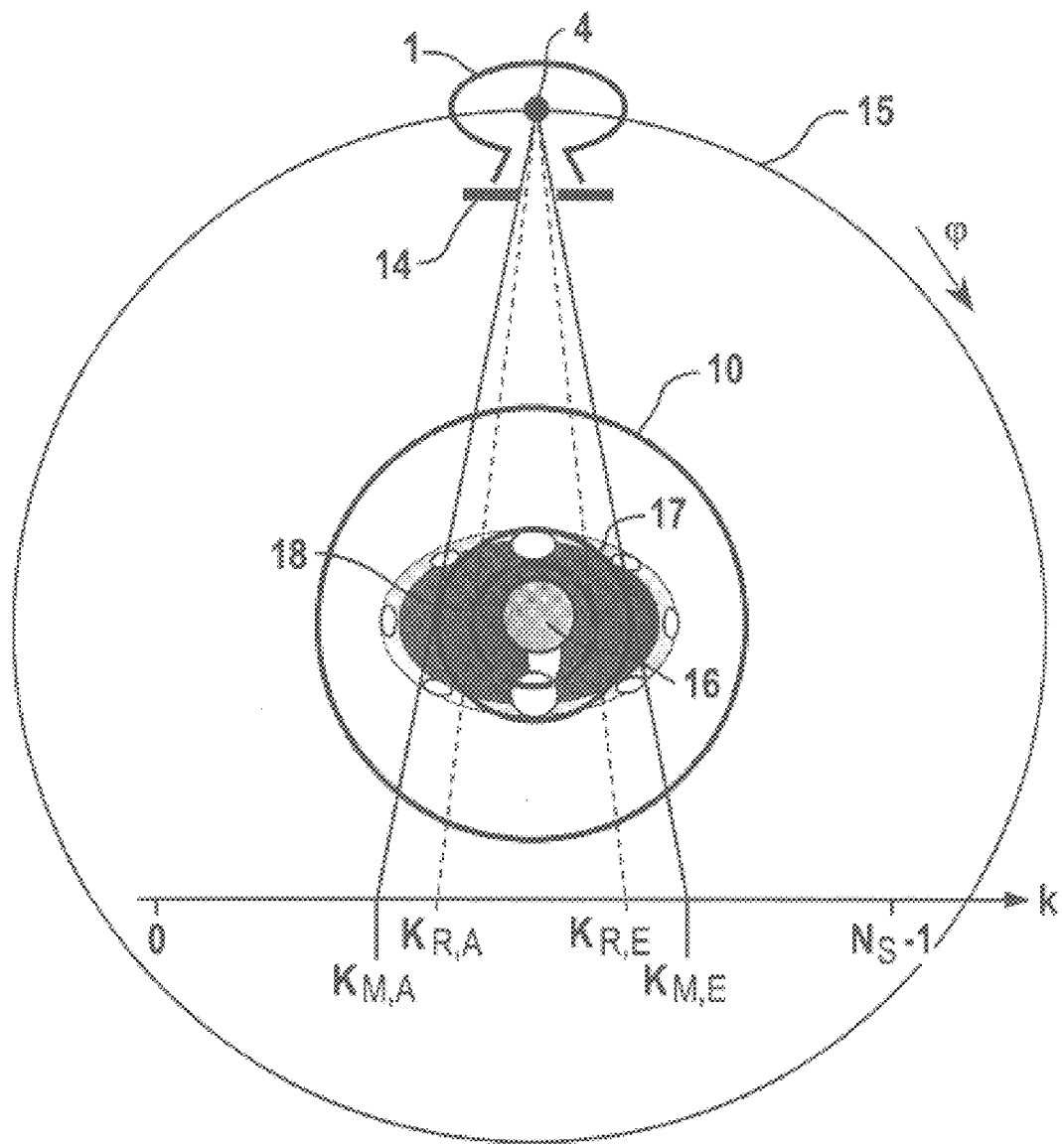

First, the reference data can be acquired at a central z position of the region of the examination subject 5 that is to be examined prior to the actual examination from a revolution around the gantry 8 with the full measuring field 10. This reference revolution can be performed with a reduced radiation dose and can additionally serve for proper positioning of the diagnostically relevant region 16 in the reduced measuring field 17. FIG. 7 illustrates the measuring process with full measuring field 17, and FIG. 8 illustrates the measuring process with a measuring field 17 that has been reduced by the primary ray diaphragm 14, at different z positions. It suffices to store the reference data in the channel region of the extrapolation interval.

Figure 9:
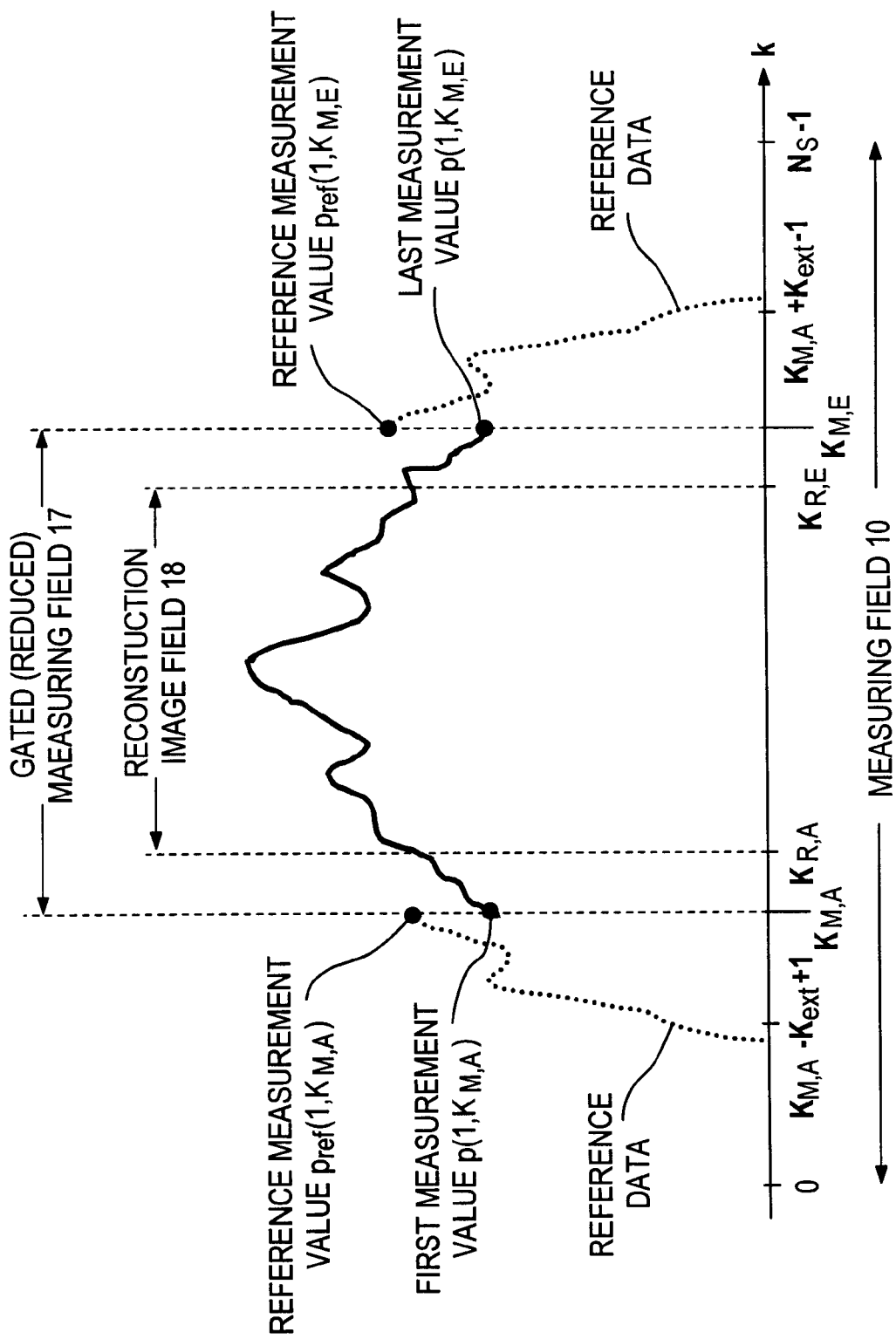
FIG. 9 shows a diagram illustrating the extrapolation of measurement points in the operating mode as illustrated in the FIGS. 7 and 8.
Figure 10:
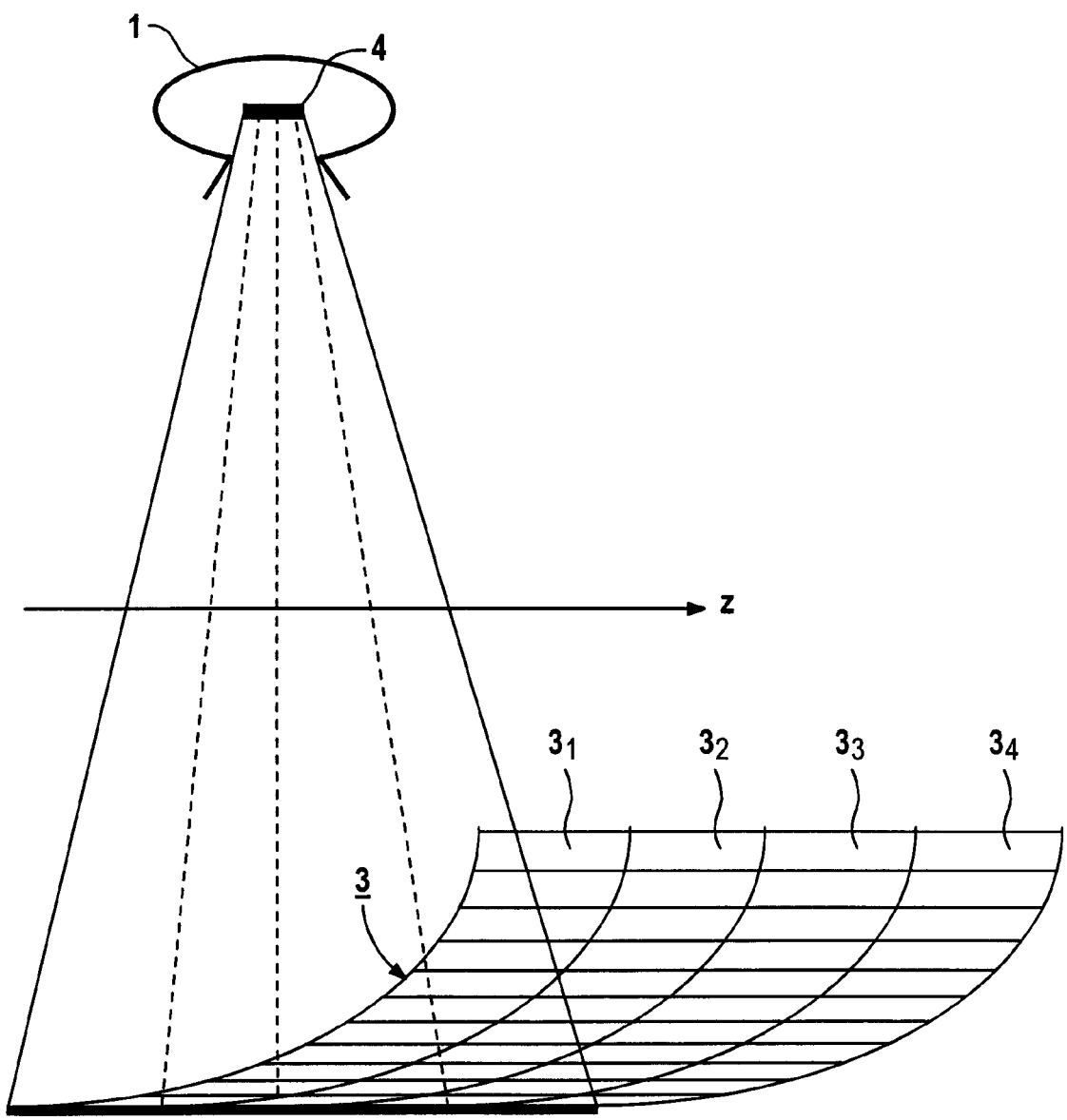
FIGS. 10 to 12 respectively show simplified schematic illustration of a CT device operating according to the inventive method, in another variation of the second operating mode.
Figure 11:
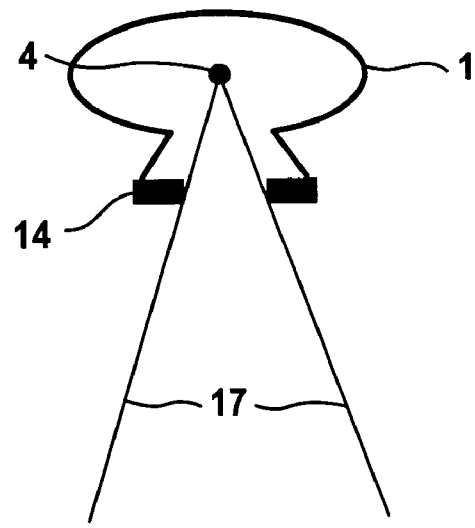
Figure 12:
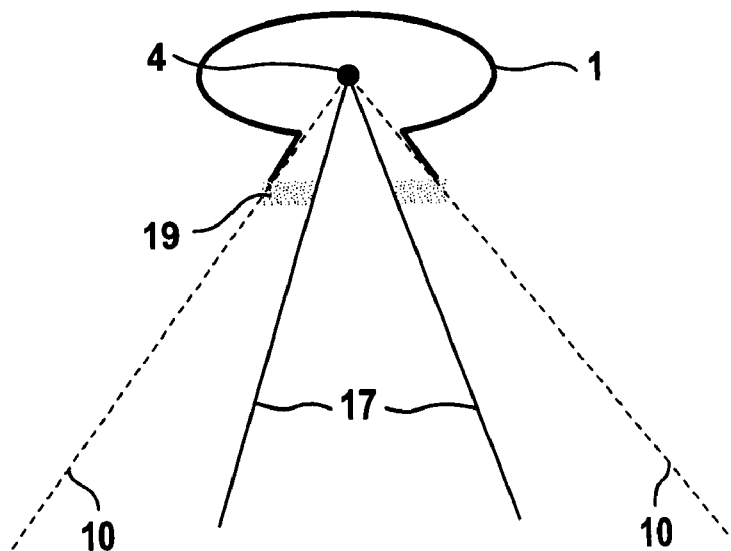

According to FIG. 9, the reference data $p_{ref}(l,k)$ of the projection at angle position I are used for purposes of extrapolating the reduced projection $p(l,k)$ during the main examination. In order to guarantee a steady transition at the limit of the extrapolation interval, the reference data are scaled with equation (13) to the level of the measured data. The scaling factors $s_A(l)$ and $s_E(l)$ derive from the ratio of the measurement values of the measured projection and of the reference projection at the extrapolation interval limits $k=K_{M,A}$ and $k=K_{M,E}$.

As in the case of the first operating mode, the extrapolation intervals are multiplied by the weighting functions $w_A(k)$ and $w_E(k)$ from equation (12) in order to achieve a smooth transition of the extrapolated data in the interval limits to zero.

$$p_{ext}(l,k) = s_A(l) \cdot p_{ref}(l,k) \cdot w_A(k), \quad k = (K_{M,A} - K_{ext} + 1)(1)K_{M,A} \quad (13a)$$

$$p_{ext}(l,k) = s_E(l) \cdot p_{ref}(l,k) \cdot w_E(k), \quad k = K_{M,E}(1)(K_{M,E} + K_{ext} - 1) \quad (13b)$$

$$s_A(l) = \frac{p(l, K_{M,A})}{p_{ref}(l, K_{M,A})}, \qquad s_E(l) = \frac{p(l, K_{M,E})}{p_{ref}(l, K_{M,E})} \quad (13c)$$

As an extension of the equations (13), for purposes of further smoothing the transition a transition weighting of the simultaneously existing measurement and reference data in the intervals $[K_{M,A};K_{R,A}]$ and $[K_{R,E};K_{M,E}]$ is performed.

Besides the acquisition with a reference examination prior to the actual examination, in a multi-line CT system such as the one herein described, the reference data can also be acquired from one specific line of reference detectors. Only in the reference detector line is there an incomplete gating of the reduced measuring field 17 at the X-ray source side so that it is possible to pick up acceptable reference data outside the limited measuring field 17, relating to the whole measuring field 10, preferably with a lower patient dose, as in the case of the described exemplifying embodiment. The dose reduction in the reference detector line can be realized by a semi-permeable diaphragm 19 at the X-ray source side, which is illustrated in FIGS. 9 to 12 for a CT device with a detector 3 having four detector lines $3_1$ to $3_4$, with the fourth detector line $3_4$ functioning as the reference line in this exemplary embodiment.

In order to reduce the storage outlay for the reference data record, it is possible to reduce the number of projections and of the data record channels prior to the storage process. The data record can then be brought back to its full size again for the extrapolation by a suitable expansion by interpolation (e.g. "Nearest-neighbor" or linear).

The extrapolation techniques described herein are presented as examples; other approaches are possible in the context of the invention. The techniques described herein, however, are considered particularly advantageous.

In the exemplary embodiment, the extrapolation occurs immediately prior to the filtering of the projections with the convolution kernel, but it is also possible in the context of the invention to perform the extrapolation at other points in the processing chain.

The exemplary embodiment relates to the medical application of the inventive method in CT technology, but the inventive method also can be applied in other tomographic imaging methods and in non-medical fields as well.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for image reconstruction in a computed tomography device comprising the steps of:

rotating a focus of a radiation source around a system axis and an examination subject disposed in a measuring field, said subject also exceeding said measuring field, to irradiate said examination subject from a plurality of different projection angles and detecting attenuated radiation from said examination subject at said different angles to form a plurality of projections, with each projection being represented by a series of measurement points, each measurement point being characterized by a channel number and a measurement value;

detecting projections in which said examination subject exceeded said measuring field;

for said projections in which said examination subject exceeded said measuring field, adding extrapolated measurement points to said series of measurement points representing the detected projection so that each series of measurement points representing a detected projection begins and ends with respective measurement points having respective measurement values substantially equal to zero; and obtaining said extrapolated measurement points by at least one of:

for each detected projection, mapping the measurement points representing the detected projection in a rectangular coordinate system having a measurement value axis and a channel number axis, and reflecting a number of consecutive measurement points at at least one of a beginning and an end of the series of measurement points representing the projection, at a first line proceeding through a first measurement point of said series of measurement points when reflecting at said beginning of said series of measurement points and proceeding through a last measurement point of said series of measurement points when reflecting at said end of said series of measurement points, said first line being parallel to said measurement value axis, and subsequently reflecting said number of consecutive measurement points at said at least one of said beginning and said end of said series of measurement points representing the projection, at a second line proceeding through said first measurement point of said series of measurement points when reflecting at said beginning of said series of measurement points and proceeding through said last measurement point of said series of measurement points when reflecting at said end of said series of measurement points, said second line being parallel to said channel number axis, and obtaining reference data measured for a measuring field which exists without gating of radiation from said x-ray source, and employing said reference data to generate said extrapolated measurement points.

2. A method as claimed in claim 1 wherein the step of detecting projections wherein said examination subject exceeds said measuring field comprises determining an average value of a number of consecutive measurement points of a projection at least one of a beginning or an end of the series of measurement points representing a projection, and selecting a threshold, and detecting the projecion represented by said series of measurement points as being a projection wherein said measuring field was exceeded if said average value exceeds said threshold.

3. A method as claimed in claim 1 comprising weighting said extrapolated measurement points with an attenuation function to cause said extrapolated measurement points to smoothly converge to zero.

4. A method as claimed in claim 1 comprising obtaining an estimated measure of said examination subject exceeding said measuring field, and selecting said extrapolated measurement points and said weighting dependent on said estimated measure.

5. A method as claimed in claim 1 comprising obtaining an estimated measure of said examination subject exceeding said measuring field, and selecting said extrapolated measurement points dependent on said estimated measure.

6. A method as claimed in claim 1 comprising reconstructing an image of a region of said examination subject from said projections using convolution having a length limit, and adding a number of extrapolated measurement points so that said length limit is intentionally exceeded.

7. A method as claimed in claim 6 comprising filtering data from said projections using a convolution kernel, and conducting said extrapolation immediately prior to said filtering.

8. A method as claimed in claim 1 comprising intentionally causing said examination subject to exceed said measurement field by gating radiation from said x-ray source to produce a reduced measuring field covering a diagnostically relevant region of said examination subject.

9. A method as claimed in claim 8 comprising reconstructing an image only of a region of said examination subect situated within said reduced measuring field.

10. A method as claimed in claim 7 comprising conducting said extrapolation using reference data for said measuring field which exists without gating of said radiation and measuring said reference data prior to obtaining projections from said examination subject in said reduced measuring field.

11. A method as claimed in claim 7 comprising conducting said extrapolation using reference data for said measuring field which exists without gating of said radiation and measuring said reference data while obtaining projections from said examination subject in said reduced measuring field.

12. A method as claimed in claim 11 comprising using a multi-row radiation detector for obtaining said reference data in the measuring field that exists without gating of the radiation and for obtaining the projections for the reduced measuring field, with each row of said multi-row detector comprising a plurality of detector elements and a channel number equal to said plurality of detector elements, and obtaining said reference data using only one row of detector elements and obtaining measurement points for the projections in the reduced measuring field using others of the rows of detector elements, and using more channels in said one row of detector elements for obtaining said reference data than in the others of said rows for obtaining said measurement points for the projections in the reduced measuring field.

13. A method as claimed in claim 8 wherein said extrapolated measurement points are obtained from said reference data, and comprising scaling said reference data to a level of measurement values of the measurement points in the projections for the reduced measuring field.

14. A method as claimed in claim 13 comprising transition-weighting said reference data to said level of said measurement values of the measurement points of the projections for the reduced measuring field.

15. A method as claimed in claim 1 wherein said extrapolated measurement points are obtained from said reference data, and wherein said reference data form a reference data record, and comprising reducing a size of said reference data record to obtain a reduced-size data record, storing said reduced-size data record, and subsequently expanding the reduced-size data record by interpolation priorto obtaining said extrapolated measurement points.

* * * * *